United States Patent
Li et al.

(10) Patent No.: US 7,637,930 B2
(45) Date of Patent: *Dec. 29, 2009

(54) MEDICAL DEVICE AND METHOD FOR TREATING SKIN DISEASE

(76) Inventors: Huanchen Li, P.O. Box 1341, Westford, MA (US) 01886; Xiaoguang Wang, P.O. Box 1341, Westford, MA (US) 01886

( * ) Notice: Subject to any disclaimer, the term of this patent is extended or adjusted under 35 U.S.C. 154(b) by 0 days.

This patent is subject to a terminal disclaimer.

(21) Appl. No.: 11/108,027

(22) Filed: Apr. 15, 2005

(65) Prior Publication Data

US 2005/0203596 A1    Sep. 15, 2005

Related U.S. Application Data

(63) Continuation of application No. 10/428,253, filed on May 3, 2003, now Pat. No. 7,537,605, which is a continuation-in-part of application No. 10/165,893, filed on Jun. 10, 2002, now abandoned, and a continuation-in-part of application No. 09/758,706, filed on Jan. 11, 2001, now Pat. No. 6,635,075, which is a continuation-in-part of application No. 09/502,992, filed on Feb. 11, 2000, now Pat. No. 6,245,093, and a continuation-in-part of application No. 09/183,639, filed on Oct. 30, 1998, now abandoned, and a continuation-in-part of application No. 08/698,323, filed on Aug. 14, 1996, now abandoned, and a continuation-in-part of application No. 08/601,196, filed on Feb. 14, 1996, now abandoned, which is a continuation-in-part of application No. 08/254,273, filed on Jun. 6, 1994, now abandoned, and a continuation-in-part of application No. 08/157,572, filed on Nov. 24, 1993, now abandoned, and a continuation-in-part of application No. 08/131,987, filed on Oct. 4, 1993, now abandoned.

(51) Int. Cl.
*A61F 2/00* (2006.01)
*A61F 7/00* (2006.01)
*A61F 7/12* (2006.01)

(52) U.S. Cl. ........................................ 607/96; 607/101

(58) Field of Classification Search .................. None
See application file for complete search history.

(56) References Cited

U.S. PATENT DOCUMENTS 1,817,823 A    8/1931    Ito (Continued)

FOREIGN PATENT DOCUMENTS

CN    90225220.8    11/1990

(Continued)

OTHER PUBLICATIONS

John C. Chato, "Thermal Therapy of Toe Nail Fungus," International Mechanical Engineering Congress and Exposition, Nov. 11-16, 2000, Orlando, Florida, pp. 1 & 2.

(Continued)

*Primary Examiner*—Robert L Nasser
(74) *Attorney, Agent, or Firm*—Mark P. White

(57) ABSTRACT

Methods and systems for treating skin disease are disclosed. Heat is applied at a controlled temperature, for a predetermined period of time, to a skin lesion associated with a skin disease according to embodiments. The temperature used, according to embodiments, is in a range between about 46-62° C., and controlled within a narrow tolerance depending upon the nature of the skin treatment.

18 Claims, 8 Drawing Sheets

U.S. PATENT DOCUMENTS

| | | | |
|---|---|---|---|
| 2,440,041 A | 4/1948 | Clark | |
| 3,325,627 A | 6/1967 | Adler et al. | |
| 3,625,202 A | 12/1971 | Oyoshirhara | |
| 3,938,526 A * | 2/1976 | Anderson et al. | 606/189 |
| 3,978,312 A | 8/1976 | Barton et al. | |
| 3,982,542 A | 9/1976 | Ford et al. | |
| 4,074,110 A | 2/1978 | Slaughter | |
| 4,090,517 A | 5/1978 | Takenaka | |
| 4,155,164 A | 5/1979 | White | |
| 4,266,556 A | 5/1981 | Barlow et al. | |
| 4,449,528 A | 5/1984 | Auth et al. | |
| 4,461,299 A * | 7/1984 | Guibert | 607/96 |
| 4,582,057 A | 4/1986 | Auth et al. | |
| 4,640,283 A * | 2/1987 | Sawa et al. | 607/89 |
| 4,657,531 A | 4/1987 | Choi | |
| 4,691,703 A | 9/1987 | Auth et al. | |
| 4,744,359 A | 5/1988 | Hatta et al. | |
| 4,747,841 A | 5/1988 | Kuratomi et al. | |
| 4,748,979 A | 6/1988 | Hershenson | |
| 4,763,657 A | 8/1988 | Chen et al. | |
| 4,878,493 A | 11/1989 | Pasternak et al. | |
| 4,907,589 A | 3/1990 | Cosman | |
| 4,944,297 A | 7/1990 | Ratkoff et al. | |
| 4,961,422 A | 10/1990 | Marchosky et al. | |
| 5,097,828 A | 3/1992 | Deutsch | |
| 5,107,832 A * | 4/1992 | Guibert et al. | 607/96 |
| 5,169,384 A | 12/1992 | Bosniak et al. | |
| 5,191,883 A | 3/1993 | Lennox et al. | |
| 5,197,466 A | 3/1993 | Marchosky et al. | |
| 5,327,886 A | 7/1994 | Chiu | |
| 5,376,087 A | 12/1994 | Haber et al. | |
| 5,445,146 A | 8/1995 | Bellinger | |
| 5,456,682 A | 10/1995 | Edwards et al. | |
| 5,459,298 A | 10/1995 | Tschakaloff | |
| 5,524,809 A | 6/1996 | Kosslow et al. | |
| 5,591,219 A * | 1/1997 | Dungan | 607/88 |
| 5,658,583 A | 8/1997 | Zhang et al. | |
| 5,662,624 A | 9/1997 | Sundstrom et al. | |
| 5,688,266 A | 11/1997 | Edwards et al. | |
| 5,830,211 A | 11/1998 | Santana et al. | |
| 6,066,164 A | 5/2000 | Macher et al. | |
| 6,091,995 A | 7/2000 | Ingle et al. | |
| 6,102,705 A | 8/2000 | Darnell | |
| 6,134,475 A | 10/2000 | Will | |
| 6,162,217 A | 12/2000 | Kannenberg et al. | |
| 6,235,027 B1 | 5/2001 | Herzon | |
| 6,245,093 B1 | 6/2001 | Li et al. | |
| 6,254,391 B1 | 7/2001 | Darnell | |
| 6,283,931 B1 | 9/2001 | Augustine | |
| 6,293,917 B1 | 9/2001 | Augustine et al. | |
| 6,303,142 B1 | 10/2001 | Zhang et al. | |
| 6,306,431 B1 | 10/2001 | Zhang et al. | |
| 6,322,583 B1 | 11/2001 | Tu et al. | |
| 6,340,301 B2 | 1/2002 | Darnell | |
| 6,340,472 B1 | 1/2002 | Zhang et al. | |
| 6,350,262 B1 | 2/2002 | Ashley | |
| 6,382,979 B2 | 5/2002 | Lindquist | |
| 6,465,006 B1 | 10/2002 | Zhang et al. | |
| 6,465,709 B1 | 10/2002 | Sun et al. | |
| 6,471,716 B1 | 10/2002 | Pecukonis | |
| 6,485,506 B2 | 11/2002 | Augustine | |
| 6,497,575 B2 | 12/2002 | Zavitsanos et al. | |
| 6,533,778 B2 | 3/2003 | Herzon | |
| 6,587,731 B1 | 7/2003 | Ingle et al. | |
| 6,589,270 B2 | 7/2003 | Augustine | |
| 6,613,350 B1 | 9/2003 | Zhang et al. | |
| 6,626,901 B1 | 9/2003 | Treat et al. | |
| 6,629,974 B2 | 10/2003 | Penny et al. | |
| 6,635,075 B2 | 10/2003 | Li et al. | |
| 6,660,029 B2 | 12/2003 | VanSkiver et al. | |
| 6,702,808 B1 | 3/2004 | Kreindel | |
| 6,708,060 B1 | 3/2004 | Avrahami et al. | |
| 6,726,673 B1 | 4/2004 | Zhang et al. | |
| 6,772,013 B1 | 8/2004 | Ingle et al. | |
| 6,780,426 B2 | 8/2004 | Zhang et al. | |
| 6,840,955 B2 | 1/2005 | Ein | |
| 6,860,880 B2 | 3/2005 | Treat et al. | |
| 6,908,463 B2 | 6/2005 | Treat et al. | |
| 7,083,613 B2 | 8/2006 | Treat | |
| 7,108,694 B2 | 9/2006 | Miura et al. | |
| 7,137,979 B2 | 11/2006 | Conrad et al. | |
| 2001/0012608 A1 | 8/2001 | Darnell | |
| 2001/0041886 A1 | 11/2001 | Durkin et al. | |
| 2002/0026133 A1 | 2/2002 | Augustine et al. | |
| 2002/0156471 A1 | 10/2002 | Stern et al. | |
| 2002/0165529 A1 | 11/2002 | Danek | |
| 2003/0023286 A1 | 1/2003 | Augustine et al. | |
| 2003/0125735 A1 | 7/2003 | Herzon | |
| 2003/0199866 A1 | 10/2003 | Stern et al. | |
| 2006/0036194 A1 | 2/2006 | Schultheiss et al. | |

FOREIGN PATENT DOCUMENTS

| | | |
|---|---|---|
| CN | 95315109.3 | 8/1995 |
| CN | 94116233.8 | 12/1995 |
| CN | 94221831.0 | 1/1996 |
| CN | 01337354.4 | 9/2001 |
| CN | 0530200072.2 | 2/2005 |
| DE | 43 31 945 A1 | 3/1995 |
| DE | 198 08 851 A1 | 11/1998 |
| DE | 197 52 282 A1 | 2/1999 |
| EP | 1231875 | 9/2004 |
| FR | 2 689 002 | 10/1993 |
| FR | 0 720 271 | 12/1995 |
| FR | 2 746 296 | 9/1997 |
| JP | 2-104351 | 4/1990 |
| JP | 5-248681 | 9/1993 |
| JP | 10-229995 | 9/1998 |
| WO | WO00/53113 A1 | 9/2000 |
| WO | WO/01/03619 | 1/2001 |
| WO | WO 01/03619 | 1/2001 |
| WO | WO03/061497 | 7/2003 |
| WO | WO03/061498 | 7/2003 |

OTHER PUBLICATIONS

R. A. Glover, et al., "Histamine release from rodent and human mast cells induced by protoporphyrin and ultraviolet light: Studied in the mechanism of mechanism of mast-cell activation in erthropoietic protopophyria," British Journal of Dermatology, 1990, pp. 501-512.

Field, S. B., et al. "The Relationship Between Heating Time and Temperature: Its Relevance to Clinical Hyperthermia," Radiology and Oncology, 1 (1983) 179-186.

Blickford, R.G., "Experiments Relating to the Itch Sensation, Its Peripheral Mechanism, and Central Pathways" Clinical Science 3:377-386, 1937.

Glover, R. A. et al., "Histamine release from rodent and human mast cells induced by protoporphyrin and ultraviolet light: studies of the mechanism of mast cell activation in erythropoietic protopophyria" British Journal of Dermatology (1990) 122, 501-512.

Treatment of Pruritus, Journal of Family Practice, 1987, vol. 25, No. 5, pp. 438.

Lowitt, M. H. MD, et al. "Pruritus" Seminars in Neurology, vol. 12, No. 4, Dec. 1992.

Medical Letter on Drugs and Therapeutics (British Edition), Consumers' Association 1966 vol. 8 No. 13 pp. 50-51.

Medical Letter on Drugs and Therapeutics (British Edition), Consumers' Association 1969 vol. 11 No. 14 pp. 60.

Ward, L., et al. "A comparison of the effects of noxious and innocuous counterstimuli on experimentally induced itch and pain," Pain 64 (1996) 129-138.

Xu and Qian, "Analysis of Thermal Injury Process Based on Enzyme Deactivation Mechanisms," 462, vol. 117, Nov. 1995.

Itch Zapper, Home Health Products, http://www.safehomeproducts.com/SHP/HH/ItchZapper.asp, Aug. 12, 2003.

SpectraClear, Symedex Medical Spa Specialists, 2003.
Sunbeam Standard Heating Pad, appearing on DRUGSTORE.COM, May 28, 2009, 1 page, Web site, appearing on: http://www.drugstore.com/products/prod.asp?pid=158396&catid=10&trx=GFI-0-RVP-10784&trxp1=10&trxp2=158396&trxp3=1&trxp4=2&btrx=BUY-GFI-0-RVP-10784.

* cited by examiner

FIG. 2A2 INTERVAL

FIG. 2A1 TEMPERATURE

FIG. 2A3 DURATION

MEDICAL DEVICE AND METHOD FOR TREATING SKIN DISEASE

CROSS-REFERENCE TO RELATED APPLICATIONS

The present application is a continuation of co-pending, commonly assigned, patent application Ser. No. 10/428,253 entitled "Medical Device For Treating Skin Itch And Rash," filed May 3, 2003, now U.S. Pat. No. 7,537,605, which itself is a continuation-in-part of patent application Ser. No. 10/165,893 entitled "Method And Apparatus For Treatment Of Skin Itch And Disease," filed Jun. 10, 2002, now abandoned, the disclosures of which are hereby incorporated herein by reference. This application is also a continuation-in-part of the application Ser. No. 09/758,706 filed on Jan. 11, 2001, now U.S. Pat. No. 6,635,075, which derives from a chain of continuations-in-part including Ser. No. 09/502,992 filed on Feb. 11, 2000, now U.S. Pat. No. 6,245,093, Ser. Nos. 09/183,639 filed on Oct. 30, 1998, now abandoned, and 08/698,323 filed on Aug. 14, 1996, now abandoned, which is a continuation-in-part of application Ser. No. 08/254,273 filed Jun. 6, 1994, now abandoned, and Ser. No. 08/131,987 filed Oct. 4, 1993, now abandoned, and a continuation-in-part of application Ser. No. 08/601,196 filed Feb. 14, 1996, now abandoned, Ser. No. 08/157,572 filed Nov. 24, 1993, now abandoned, and original application Ser. No. 08/131,987 filed Oct. 4, 1993 now abandoned. The earliest filing date of this application is hereby claimed.

TECHNICAL FIELD

This invention relates to methods and devices for the treatment of inches, rashes, and skin-diseases, and particularly to such methods and devices which effect such treatments by the application of heat at specific temperatures and for specific periods of time.

BACKGROUND OF THE INVENTION

Doctors know that UV light relieves psoriasis and eczema, but how? Use activated vitamin D did not give the same effect. It is now known that UV activates a group of genes called stress-genes, which produce stress proteins. These proteins are responsible for keeping the skin healthy and beautiful, and effectively clear up skin problems. Since UV can also cause DNA damage, skin-cancer and skin aging, it is not the ideal means to activate stress-genes. Many other forms of energy have been found to be not only more powerful than UV in activating stress-genes, but also more effective at clearing up skin problems.

Since heat is the safest energy, it does not cause DNA damage, or skin-cancer, and it is the most effect one in activate stress genes. Also, since the heat destroys toxins below the surface of the skin and shows the best results in clearing up skin-problems, the present invention is intended for the treatment of skin itch, skin rash, and related skin diseases by means of the controlled application of heat.

The use heat in the treatment of skin diseases has been known for a long time folk remedies using heat exist in many different cultures, and the origins of these remedies are often obscure.

However, the use of heat in the treatment of skin itch and rash is different from such treatment for other skin problems. An article in the British Journal of Dermatology 122(4):501-12, 1990, by Benee A Glover, Cynthia S. Bailey, Kim E. Barrett, S. I. Wasserman and Irma Gifli, of the Division of Dermatology and Allergy Department of Medicine, University of CA, San Diego School of Medicine, San Diego, Calif. entitled: *Histamine release from rodent and human mast cells induced by proloporphyrin and ultraviolet light: studies of the mechanism of mast-cell activation in erythropoietic protoporphyria.*, deals with just this issue. In a study reported therein, it was found that heating or prolonged heating at temperatures lower than 45° C. exacerbates skin itch and rash, but does not have any detrimental effect on most other skin problems. Those temperature ranges found effective against itch and rash are generally in excess of 49° C., Sufficiently hot to result in pain if applied to the skin for more than 3 seconds.

Furthermore, for treating itch and rash the temperature must be maintained at the superficial surface, that is not deeper than dermis where the mast cells are located. This must be done without burning the skin, or causing excessive discomfort. The mast cells must be inactivated, but the inner part tissues such as blood vessels must be maintained at a safe temperature, thus avoiding edema and pain. This is so whether or not the inactivation of mast cells is the sole mechanism for stopping itch. There is some variation of the best effective temperature for treating itch and rash, depending on factors which are discussed below.

The inventor has found that different types of itches and rashes require different treatment temperatures. These best effective temperatures depend, inter alia, on whether the patient being treated is a child or an adult, and women or men, etc. All of the treatment temperatures required, however, are within a range of about 10° C. It has been found that the use of these best effective temperatures, to within a tolerance of plus or minus one-half, effectively avoids side effects, such as edema and rebound of itch. And, for some adults, temperatures below 49° C. should be avoid, as they worsen itch and rash, rather than providing relief. For some toddlers, temperatures above 49° C. should be avoid, as they are too hot. These toddlers will not allow you to apply such a heat, and in the case of a metal heater, for enough time, such as for at least 1-2 seconds, that is required to heat the dermis to the effective temperature. Therefore, the mast cells cannot be inactivated and the itch will be worsened. Temperatures around 49+/−0.5° C. have been fond optimum for most children, as have temperatures of 51.5+/−0.8° C. for adults, and of 47+/−0.5° C. for toddlers and some temperature sensitive women, in the case of itch. The temperature needs better control for temperature sensitive people, and areas, than for normal people. A variation of +/−0.25° C. or even narrower may be better for them.

Different parts of the body have also been found to have different best effective temperatures. For example, 50° C. is the best temperature for a child or an adult face, 52° C. for adult body and arm skin, and 54° C. for adult leg skin. If 50° C. is used for adult leg skin, which is thicker than the face skin, the itch will not be stopped, and side effects, such as edema and rebound of itch, may result. Furthermore, best effective temperature is also dependent upon the rate at which the skin is heated, and for that reason best effective temperature may change with a change in the material actually in contact with the skin. The above temperatures are for a planar steel heating surface, with a 9 volts and 350 mA power supply. Different power supplies may also cause the best effective temperatures to change.

New versions of the device are in development which will allow regulation of the temperature to take into account personal variations of the best effective temperature.

Experimental results, as well as the report of Glover, et al., Id, make it clear that the heating time of the skin should be as short as possible, while still receiving the benefit required.

Thus the direct contact of the heating element to the skin provides the most direct method to effect an optimum treatment of this nature. This direct contact is accomplished in the present invention by a circular metal heat transfer surface of approximately one inch diameter. The direct contact also provides an advantage in controlling the speed to heat up the skin. Some materials can control the amount of heat to pass to the skin in a timely manner. They will be used as the skin heater, or be put on the surface of the skin-heater, so as to heat the skin to the desired temperature in a desired time. This will avoid the pain and effectively clear up the itch. The reason for this is because if the skin is heated up too fast, pain will result, and if heated too slowly, the itch will worsen.

At present, there exist a number of commercially available heating pads that apply heat to the skin for therapeutic purposes. However, none of these is effective against skin itch and rash, because none of them accurately and precisely apply the required temperatures for treating itch and rash. These heating pads are intended to heat a large area of the body for more than 20 minutes. They have to provide temperatures not significantly higher than 43° C., otherwise, they will cause burning. There are also commercially available devices like our Electronic Itch Stopper which is available at http://www.ItchStopper.com. They are all covered by our prior applications before they came on the market.

Other apparatuses that are already known to heat the skin for therapeutic purposes are as described, for example, in the documents of U.S. Pat. No. 4,763,657 (Chen); U.S. Pat. No. 4,657,531 (Choi); and U.S. Pat. No. 4,907,589 (Cosman). None of these have provisions to precisely control and maintain temperature, as required of the current invention. It is so obvious that U.S. Pat. No. 4,090,517 (Takenaka) cannot provide a specific and a narrowed temperature, which is essential for skin itching problems and required of the current invention.

Other old methods of heat treatment for skin ailments include the use of scalding water to heat the skin to stop itch. This method obviously can not be done with the amount of control required to effect the best effective temperature, or with control of the time of application. For these reasons, this method has been abandoned.

Our invention has shown great success both in our clinical trials and in practical use by consumers in the treatment of insect bites, psoriasis, eczema, acne, hives, poison ivy/oak, dermatitis, allergic skin itching, renal failure skin itching, hepatitic skin itching, and all other skin itches. It erases the itch in seconds, and clears acute and chronic skin problems quickly.

The apparatus disclosed in detail below is both practical and economical to use. In addition to its preferred forms it may be made in a variety of sizes and shapes.

The device includes easy-to-understanding instructions which specify the best effective temperature for a variety of skin conditions, skin types, and ages. A light indicator located on the body of the invention flashes when the heater reaches the predetermined temperature commanded by the temperature selector, and the user is instructed not to apply the heater until this indicator flashes. In alternate embodiments, a sonic signal is used to indicate that the devices has reached its operating temperature.

A further alternative embodiment includes a heating surface which repetitively retracts and extends. This automatic intermittent application of the heater is especially important when higher temperatures are required for the treatment, since higher temperature require shorter application times, repeated at short intervals.

Because the effective temperature against itch can be so high as to be intolerable if applied for longer than 3 seconds, means are provided to heat the skin to the effective temperature range, such as 52° C., for about 2 seconds and then let it cool down to a tolerable temperature, such as 47° C., for about half second. This process is repeated for between one to ten minutes in order to cure skin diseases.

BRIEF SUMMARY OF THE INVENTION

The invention is to make a heating apparatus work on skin itching, and other problems. Our apparatus has two unique features. First, the apparatus can provide a specific temperature such as 50° C. Second, the temperatures is substantially unique which means its variation is so narrow as to work for a unique case. It is a further object of this invention to provide such an apparatus which is simple, inexpensive, and portable.

An array of apparatus each comprises heating means providing one single predetermined specific temperature inside the range of about 46 to 62° C., the heating means are capable of raising the skin to the temperature within a desired time such as within 10 seconds or 20 seconds, and maintaining it at that temperature, control means to control the heating means temperature within +/- about 2° C., 1° C., 0.5° C. or even 0.25° C. depend on specific treatments, a power source means to provide enough energy for the heating means. All of these are contained within a housing comprising a contact end, with the heating means positioned in the contact end. Each kind of apparatus in this array will provide a substantially unique temperature for a specific treatment, such as one provides 47+/-0.5° C. for children, and another provides 51+/-0.8° C. for adults.

A more complicated one, in addition to the above means, comprises temperature selection means within the range of 46 to 62° C. The above heating means can provide any single temperature in 46 to 62° C. The selection means is also contained within the housing and are accessible to the user.

According to a second aspect of the invention, the apparatus further comprises a substantially planar heat transfer surface located at the contact end, heated by said heating means. This surface is substantially circular, with a diameter of at least one-half inch. Material that allows a desired amount of heat to pass to the skin in a desired time may be used as the planar, or be put on the surface of it.

According to a third aspect of the invention, the apparatus further comprises signaling means to indicate that the user's skin is at the selected temperature, as well as means to select one of a multiplicity of temperatures, each such temperature comprising a best effective temperature for a particular treatment, and comprising means to control skin temperature to within one-half degree centigrade.

According to a forth aspect of the invention, the heating means further comprises a slideably moveable heating surface positioned within the contact end, said heating surface having an extended position in which the surface is in contact with the skin of the user and a retracted position out of contact with the skin. Also included are means to position the surface at either position, and selection means to control said motion.

According to a fifth aspect of the invention, the positioning and selection means provide a periodic motion of the heating surface, and the selection means provides control of frequency and duty cycle of said motion.

According to a sixth aspect of the invention, the apparatus further comprises means to select one or more additional temperatures, so that, when cyclical operation is selected, heat will be alternately be applied first at the first selected temperature, then at the second selected temperature, and so on until all the selected temperatures have been applied in sequence, then at the selected temperature, and repeating indefinitely.

According to a seventh aspect of the invention, the apparatus further comprises a grid at the contact end, said grid having a multiplicity of apertures. The heat transfer surface contains a multiplicity of protrusions which extend through the grid apertures when the surface is in extended position.

BRIEF DESCRIPTION OF THE DRAWINGS

These, and further features of the invention, may be better understood with reference to the accompanying specification and drawings depicting the preferred embodiment, in which.

DETAILED DESCRIPTION OF THE INVENTION

A number of preferred embodiments of the invention are discussed in this section.

Figure 1:
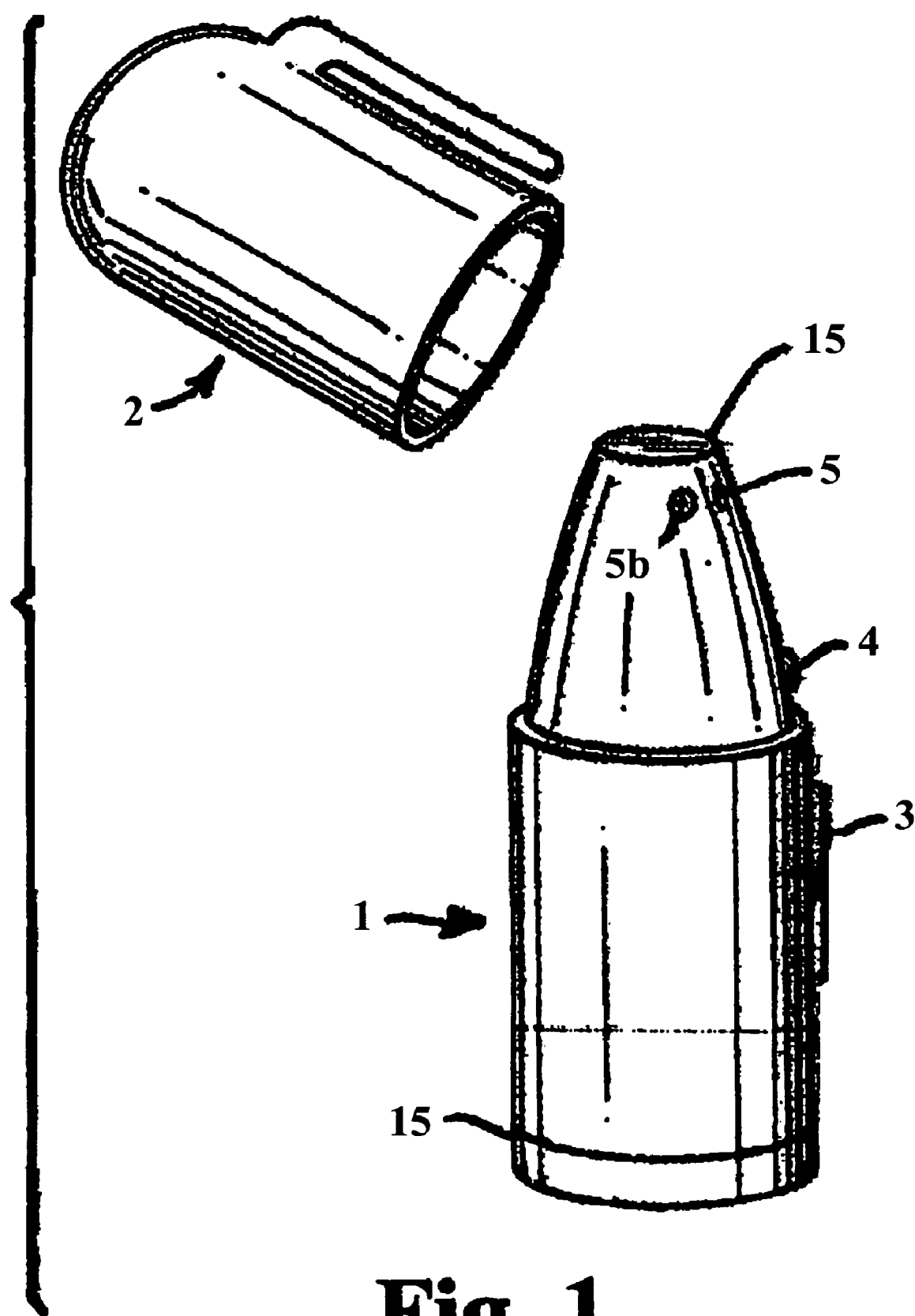
FIG. 1 is a perspective view of the present invention in its first preferred embodiment.

The first preferred embodiment of the apparatus may be understood by referring to FIG. 1, showing the invention is in the form of a hand-held apparatus with self-contained power supply by means of commercially-available batteries. The apparatus includes an optional protective cap 2 and a housing 1 which contains all the remaining components of the invention. A temperature selector 3 is located half-way up the body 1. This selector is of a rotary type which selects the best effective temperature in 1 degree-centigrade increments, to within one-half-degree centigrade. A main power switch 4, turns power on and off. Light indicator 5 illuminates when the selected temperature has been reached, and light indicator 5b illuminates when power is on. Heat is applied to the skin through the heat application surface 6a. A temperature transducer 9 (shown in FIGS. 1B & 2), thermostat 7 (FIG. 2), are located directly adjacent to the heat application surface, so that the temperature detected is essentially that of the user's skin during application. The batteries 17 (FIG. 1B) which serve as the power source 8 (FIG. 2) are located within lower portion of the housing. Batteries are replaced by means of a screw-on cap 15, at the bottom end of the housing.

In the case of an array of apparatus, we will remove the above the temperature selector 3 and make each kind of apparatus in the array to provide a single temperature.

The temperature selector 3 is used in such a manner as to enable users to directly select one best effective temperature for the heater. It provides for selection of two or more predetermined temperatures. Different versions of this embodiment are provided for different ranges of temperatures, depending upon general application.

The heat application surface may be made of a number of different materials. A heat conductive metal is one of the preferred materials, especially when used in conjunction with a magnetic-induction type heater, as is the case with the first preferred embodiment. The surface may alternatively be covered by a non-heat-conducting coating, or material, such as a thin layer of rubber, in order to reduce pain by reducing the conduction speed of the heat to the skin. Many users are more comfortable when the temperature rises gradually to the best effective temperature. Such a gradual temperature rise is found to be equally effective as a rapid rise, in regard to the curing of skin itch and rashes.

Figure 1B:
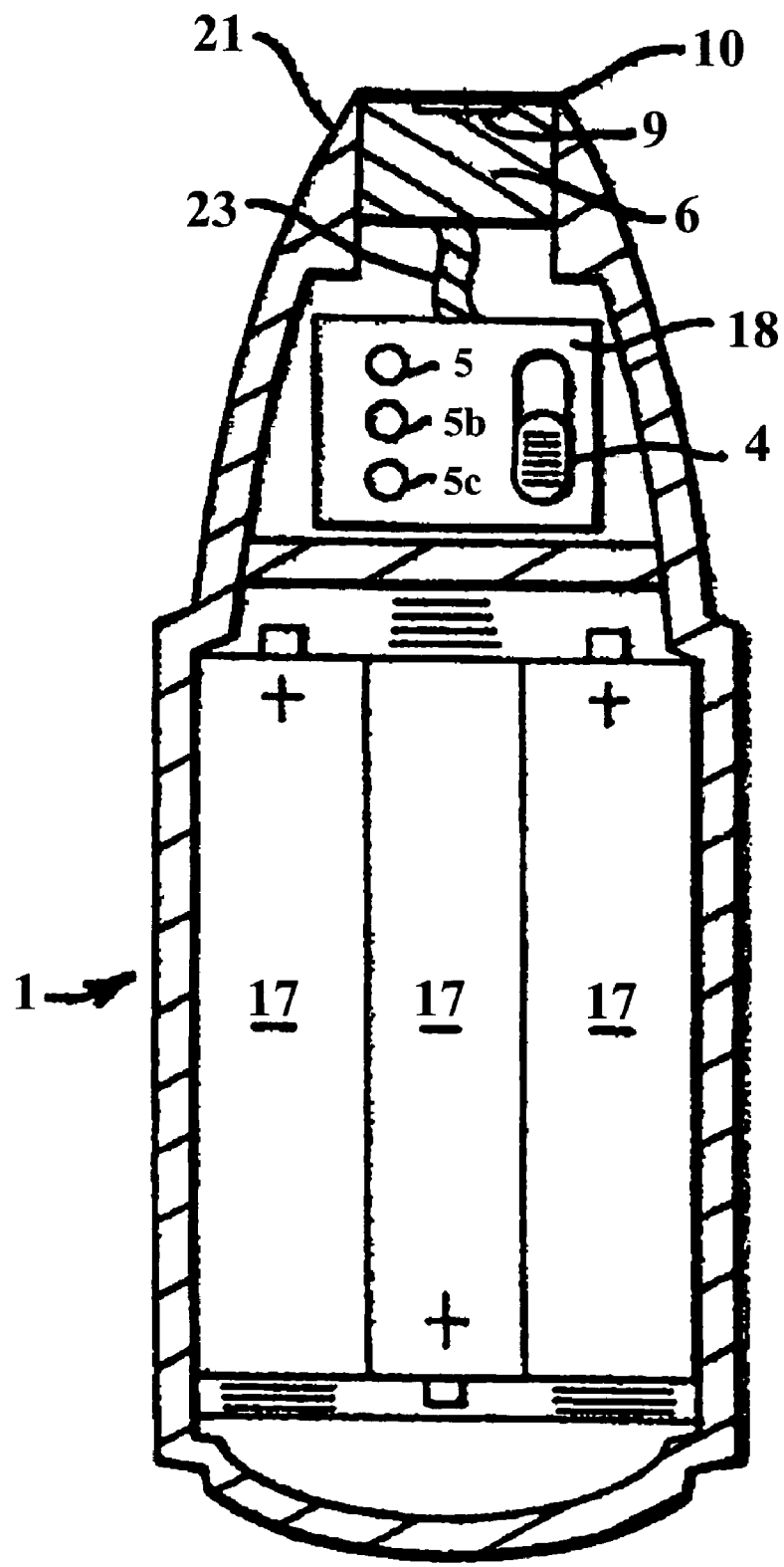
FIG. 1B is a cross-section view of the model SM version of the invention, a variation of the first preferred embodiment.

A variation of the first preferred embodiment is shown as FIG. 1B, and corresponds to a commercially-offered version of this invention, model SM, as mentioned above. In this cross-section view, the batteries are show as the commonly used "AA" cells, with three such cells 17 mounted within the housing 1 as described above. The electronics used to control the device are mounted on circuit board 18, located in the upper part of the housing as shown. In model SM, there is a third indicator light 5c, mounted on the circuit board together with indicator lights 5 and 5b. In this implementation, the indicators represent "Ready"5, "Child 5c", and "Adult"5b. In the implementation of FIG. 1B the switch 4 has three positions, corresponding to off, "Child", and "Adult". The Adult and Child switch positions correspond to two different temperatures, thought to be optimum for eczema and psoriasis, for children and adults, respectively. When either Child or Adult position is selected, the Ready light indicates that the apparatus has reached the selected temperature. In this embodiment, the heat application surface presents a flat, circular surface flush with the contact end of the housing, as shown in FIG. 1B. This surface has a diameter of approximately ⅜ inch.

The heating transfer surface in this embodiment is combined with the heating element itself in one integral unit. The circuit board contains control electronics which supplies current to the heating element through cable 23 when the temperature sensed is below the temperature commanded by temperature selector 3. If the temperature reaches or exceeds the temperature commanded, the current is discontinued. The control electronics provide a smooth response profile (i.e. temperature vs. time), with a minimum of overshoot, to a precision of plus or minus one-half degree centigrade.

A second commercially-available version of this invention, Model LD previously described, is very similar to this first preferred embodiment, except that Model LD has a cord allowing the device to plugged into a normal household utility outlet. The heat transfer surface in this version is metal, and presents a flat, circular plate flush with the contact end, as in Model SM. However, the diameter of the surface in Model LD is approximately one inch. This greater surface area allows application to a larger skin area, and is facilitated by the high power available from using house current as a power source.

Model LD also provides only two indicator lights, indicating "ON/OFF", and "READY". Current version of the Model LD allows 5 temperature selections with the temperature selector.

In one of the variations of this first preferred embodiment, the selector switch allows the user to chose one of many different discrete temperatures within the range of the apparatus. This switch is used in place of the three-position switch of FIG. 1B, and is shown in FIG. 2A1. The switch contains a rotor 19, with a pointer 20 to indicate which of the positions is selected. The switch has allowing the selection of one of the temperatures indicated, with one of the positions being "OFF". Only two indicator lights are used in conjunction with this variation: "ON" and "READY." Illumination of the "READY" indicator indicates that the apparatus has reached the selected temperature.

Figure 3:
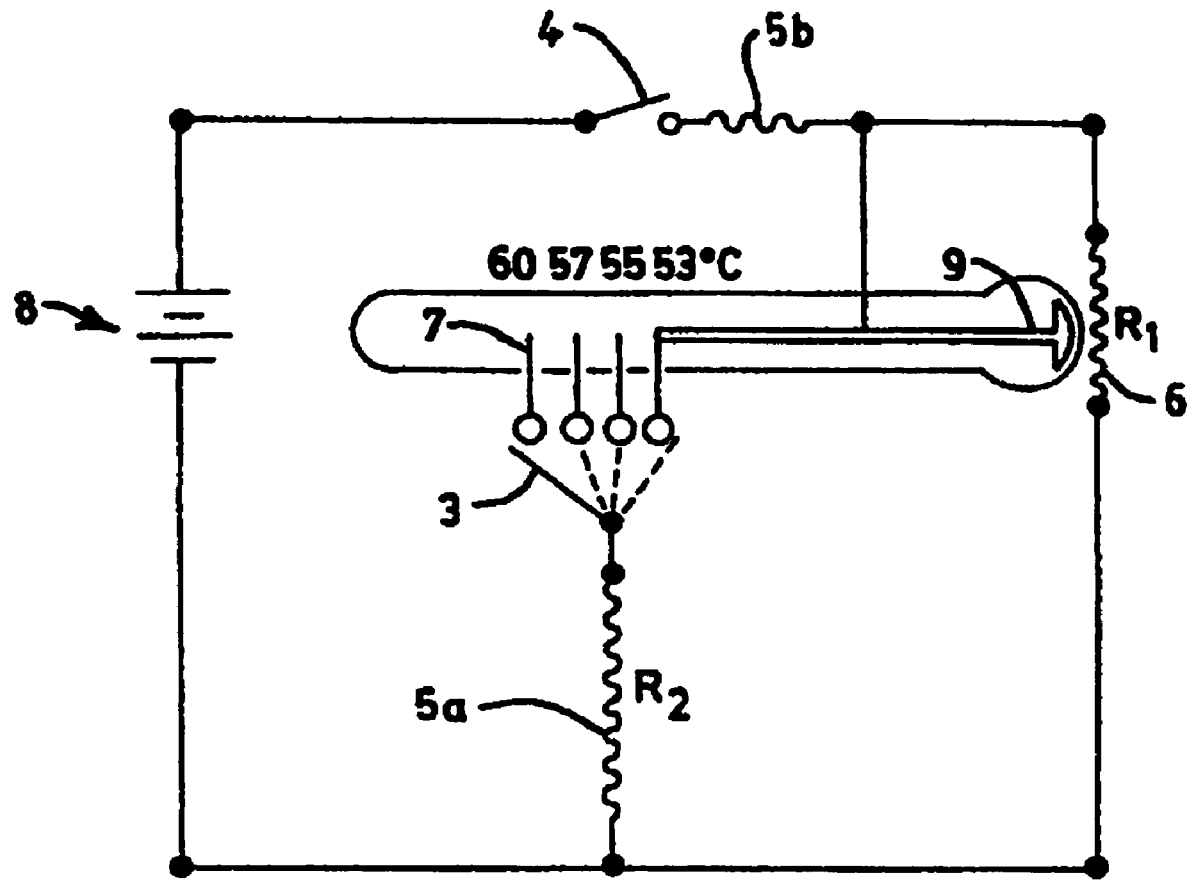
FIG. 3 is a block diagram of the electronic circuit for the temperature probe/thermostat embodiment of the apparatus.

The electronic implementation of the apparatus can take many forms. Many different methods of heating are available, and the art of heat control systems for small appliances is well developed. FIG. 3 depicts the operation of the apparatus in one implementation in the form of an electrical schematic. The power source in the form of a battery 8, is connected through switch 4 in series with indicator light 5b to the temperature transducer 9, and heater 6. The multi-position switch 3 selects one of several contacts which detect different positions along the transducer corresponding to different temperatures. When the selected temperature is reached, the transducer makes an electrical connection with the rest of the system, allowing the "READY" indicator 5a to illuminate. The temperature transducer in FIG. 3 is temperature probe 9 filled with mercury. When the heater is at lower than the selected temperature, the thermostat allows the maximum current to go through the heating element. When the heater reaches the selected temperature, the mercury will serve as a conductor to divide and therefore reduce the heater current, thereby reducing it sufficiently to maintain the selected temperature.

Figure 2:
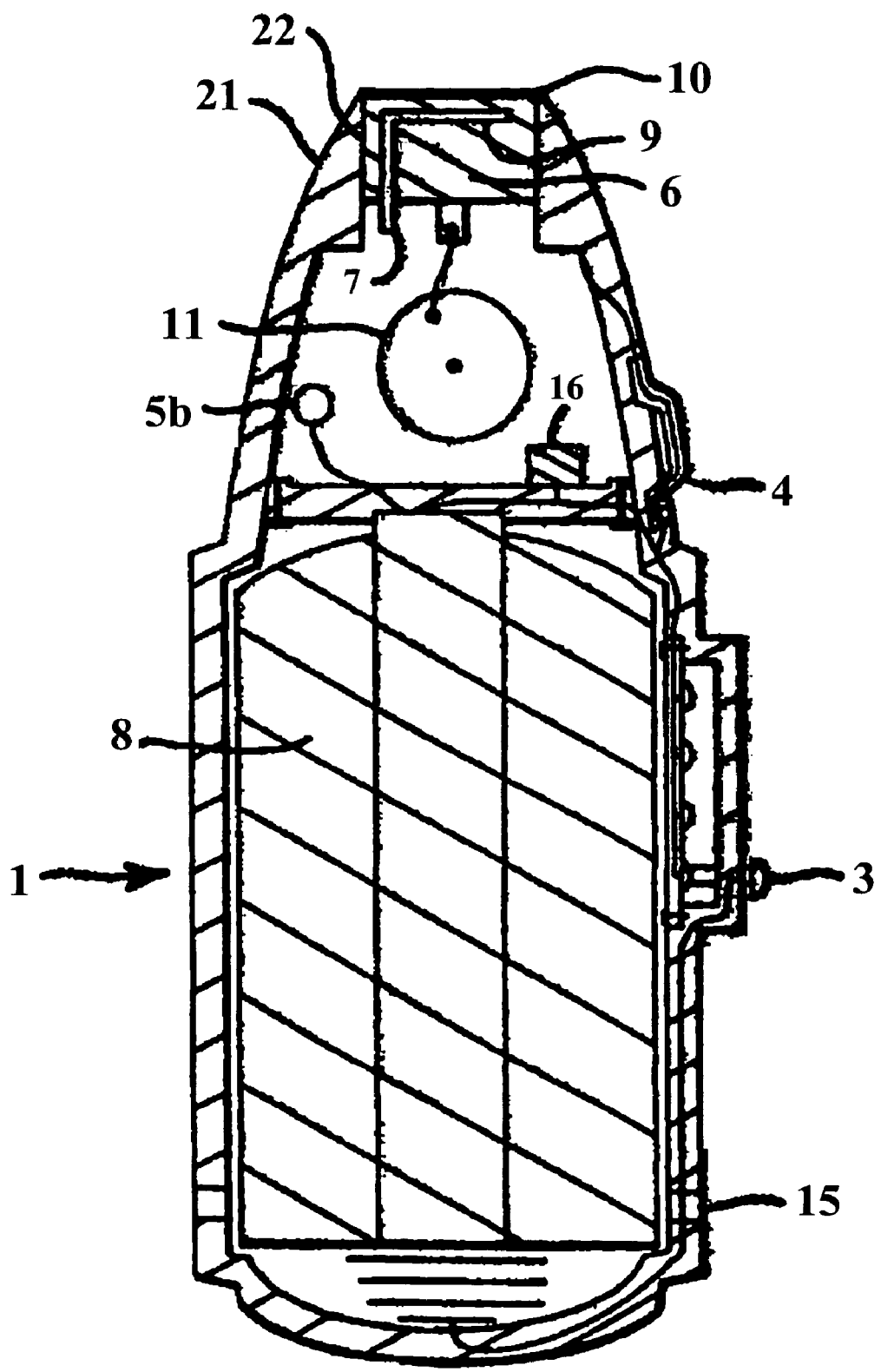
FIG. 2 is a section view of the mechanical pulsation embodiment of the invention.
Figure 2A:
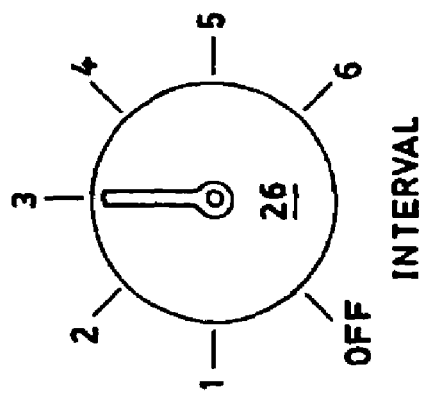
FIG. 2A is a plan view of the selector switches (2A1-2A3) used to control temperature selection, and operation of the mechanical pulsation and indirect heating embodiments.
Figure 2A:
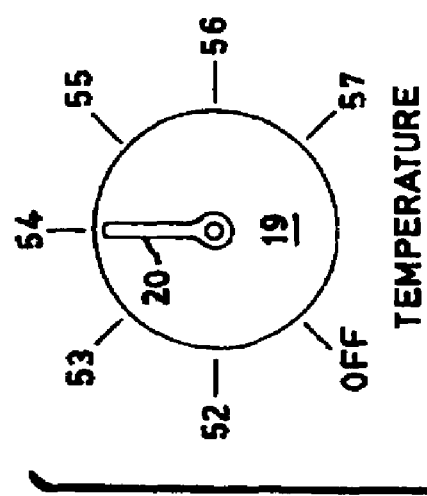
Figure 2A:
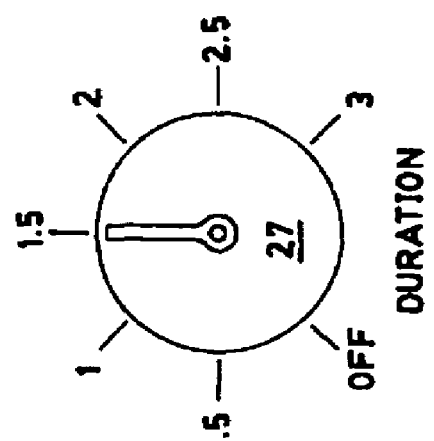

A second preferred embodiment of the current invention is depicted in FIG. 2. In this embodiment the heat transfer surface/heater combination is slidingly mounted in a channel 22 within the contact end of the apparatus. The heater has an extended position, in which the heater is in contact with the skin of the user, and a retracted position in which the heater is withdrawn within the channel. The heater is driven between its two positions by a positioning mechanism 11, which consists of a motor/crank combination in this embodiment. An alternative variation uses a solenoid as a positioning mechanism in place of the motor/crank actuator.

In this embodiment the temperature selection/detection control moves the heater against the skin of the user, and away from the skin in a repetitive manner, at a rate controlled by the user by means of two selector switches. One such switch controls the rate at which the heater moves against the skin, in seconds per cycle, as depicted in FIG. 2A2. The second switch controls the duration of the application, in seconds, as depicted in FIG. 2A3. The ratio of the duration of the application to the time between applications is called the "duty cycle".

It has been found that such a pulsating application of heat is better tolerated by many users than a prolonged application of heat in constant contact with the skin. Toleration varies widely from one individual to another. This embodiment allows users to regulate the duty cycle of the application to suit their individual needs.

A variation of this embodiment includes a grid 10 at the contact end of the apparatus, and in contact with the skin of the user during application. The heat application surface contains raised projections which mate with the grid, and protrude through the grid when the heater is in the extended position, so that these projections are in contact with the skin in this position. This grid provides a safety mechanism when the heating element is retracted. It also allows the temperature detector to be located in the grid itself, which is in contact with the skin, thus providing an more accurate measure of skin temperature.

Figure 4:
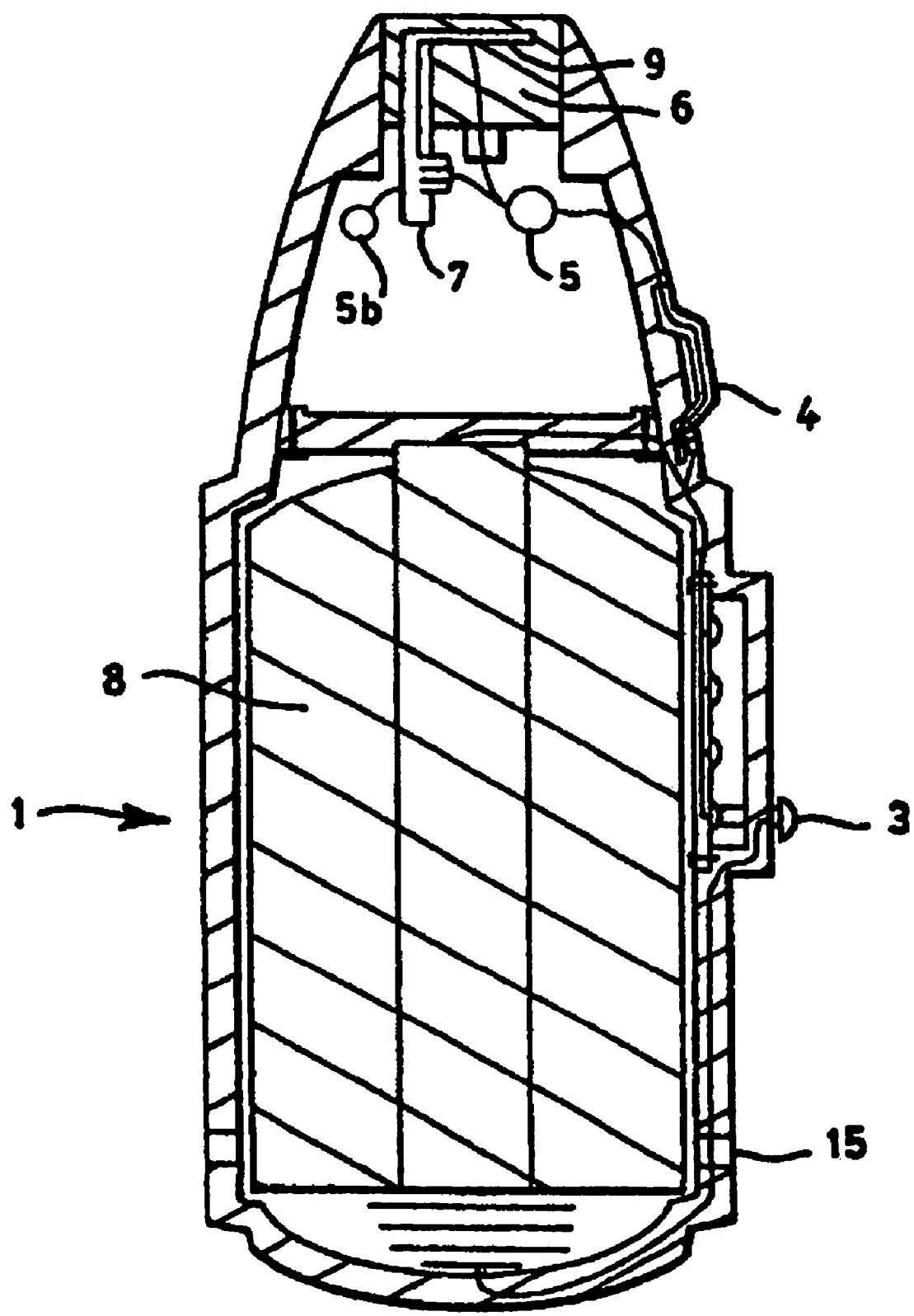
FIG. 4 is a section view of an alternate version of the temperature probe/thermostat embodiment, with alternative location of the thermostat.

The third embodiment as shown in FIG. 4 that omits the positioning means 11 and the grid 10 of the above mentioned embodiment. In this case, a light indicator 5 that will be turned on or will flash or will change color after the heater reaches the selected temperature will be included in this apparatus to replace the omitted elements 10 and 11 to ensure only said best effective temperature is used. Also in this case said heater is fixed at said contact end and said intermittent application of heat is performed manually. It would be possible to omit the light indicator 5 if a strong and stable power source, together with a good heat-transfer material for the heat transfer surface are used, providing rapid heating of the transfer surface to the desired temperature, and maintaining of that temperature.

The fourth embodiment as omits the temperature selector of the second embodiment. In this embodiment the heater is fixed at one exact best effective temperature, selected for a specific skin condition.

Figure 5:
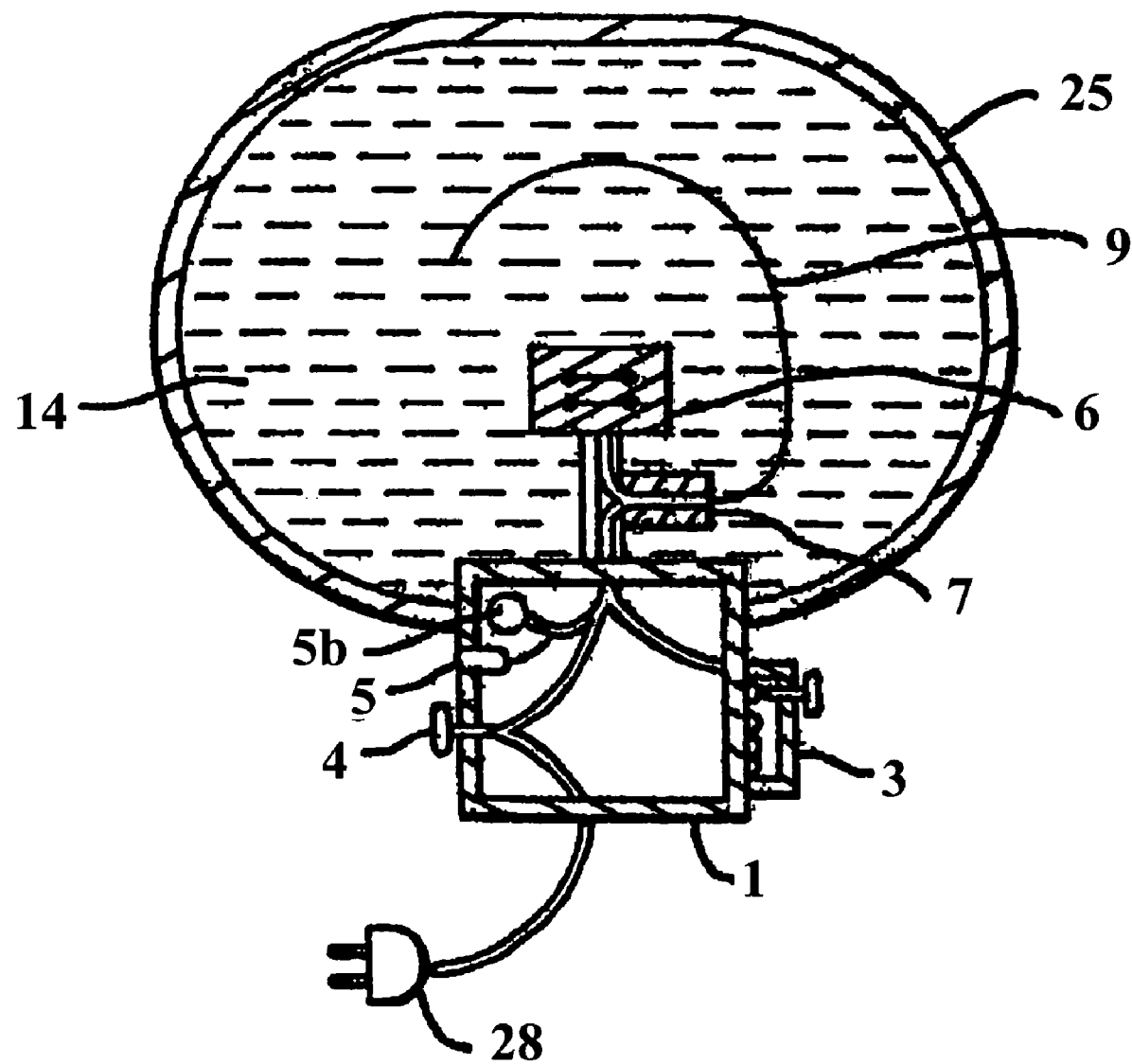
FIG. 5 is a section view of the liquid-filled heating surface embodiment.

In a fifth embodiment, as shown in FIG. 5, a heat-conducting liquid is used to maintain the temperature within the heat transfer surface which contacts the user's skin. The liquid used is preferably one with a high specific heat, such as oils of various types. The material need not be liquid at room temperature, so long as it liquefies at the best effective temperature. The advantage of this method is that the temperature and the sensing device may be located at any point within the liquid, or in proximity to the liquid, simplifying the design and manufacture of the apparatus. The high specific heat of the liquid, as well as the mobility of the molecules within the liquid, produces a uniform temperature within the body of the liquid. In contrast, metals may exhibit a thermal gradient between the area in proximity with the heater and the area in proximity with the skin, making accurate temperature control more difficult. Referring to FIG. 5, the heating element 6 is immersed in the heat transfer liquid 14, while temperature is sensed by the transducer 9, also immersed within the liquid. The liquid is contained within the heater head 25, which may be flexible or semi-rigid. A flexible material provides the advantages of allowing application of heat to a non-planar area of the skin, such as the shoulder or face. The heater head may be made of any material, such as plastic or rubber, which is soft to the touch and does not abrade the skin, the head is of a generally spherical, or ellipsoidal shape.

Still referring to FIG. 5, the remainder of this embodiment is similar to the first preferred embodiment. An external power source is used, as indicated by the utility plug 28. Indicator lights 5 and 5b are used to indicate power on, and "READY", as in previous embodiments. A multi-position selector switch 3 is used to select one of several best effective temperatures. Because of the use of an external power source, the heat transfer surface may be significantly larger than in the embodiments powered by self-contained batteries.

Figure 6:
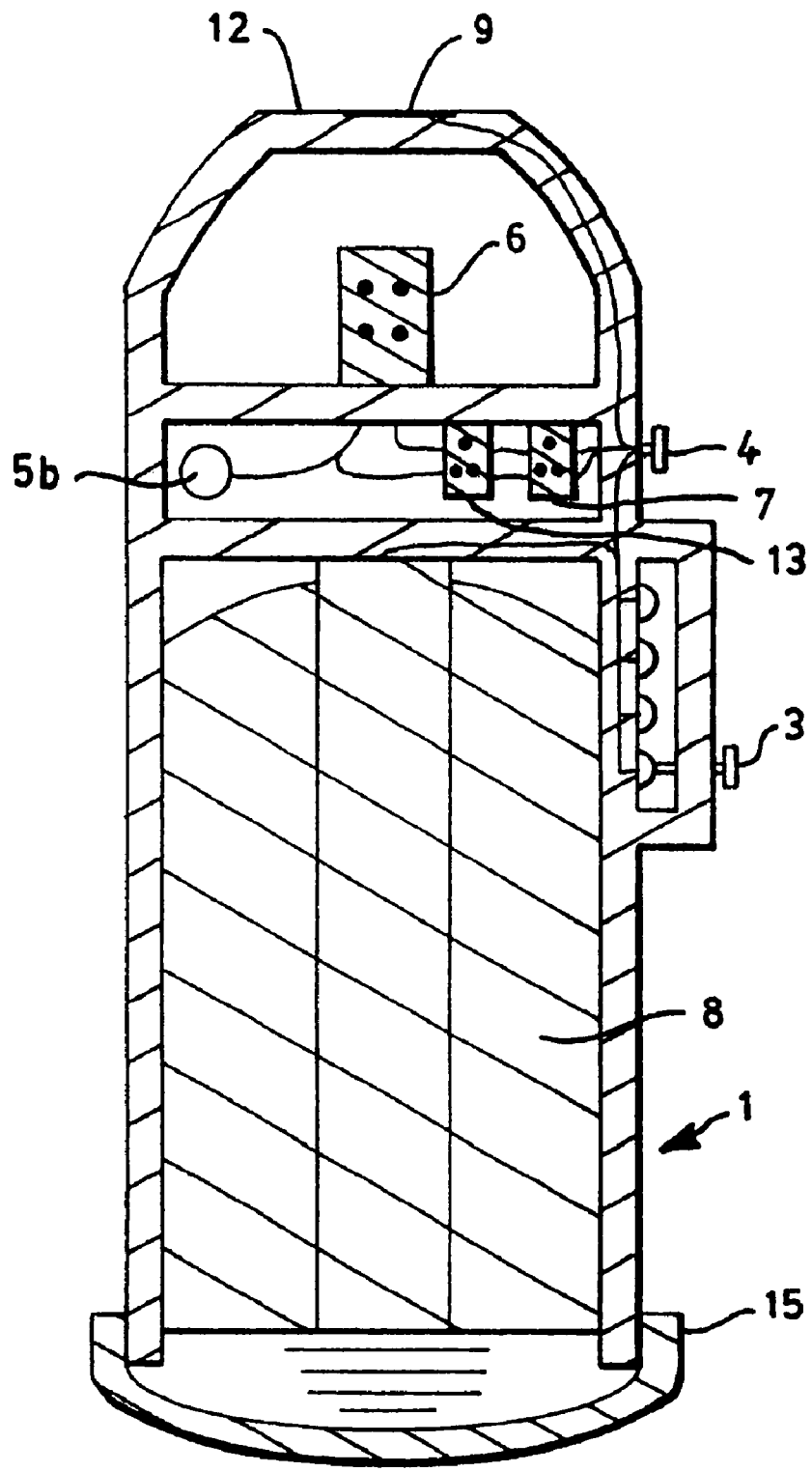
FIG. 6 is a section view of the indirect heating element embodiment.

In a sixth embodiment, as shown in FIG. 6, laser, microwave, sonic sound, and infrared radiation may also be used as a heat source for this invention. Such indirect heat sources require special means to detect heat at the surface of the skin. One recommended method is to incorporate the temperature transducer in a wall means 12 located at the contact end of the apparatus, as shown in FIG. 6, which depicts a sixth preferred embodiment of the invention. In this case, the heater source will be set behind the opening at the contact end. The heater should provide a heating energy that is high enough to heat the skin to an effective temperature within about 1-2 seconds. A wall means 12, such as a grid, is located at this opening to prevent direct contact of the skin to the heat source 6, as well as to prevent the user from accidentally placing his fingers, or other objects, in contact with the heat source burning. In this embodiment, the temperature transducer 9 should be located within the wall means, in order to accurately measure the temperature at the skin of the user.

This embodiment further provides intermittent heating means without requiring a position control mechanism. Intermittent application of the heat to the skin by this method is done by switching the heat source on and off, an alternative method to that of the second preferred embodiment, which uses motor-crank mechanism, or solenoid to physically move the heat transfer surface against the skin, and periodically retract the surface. In the seventh embodiment, the apparatus includes a selector switch allowing the user to vary the duty cycle of the heat application, similar to that of the second preferred embodiment. The temperature transducer located in the wall means senses the temperature at the surface of the skin, and controls heat source so that the skin temperature reaches the temperature commanded by the temperature selector switch 3 at the times commanded by the duty cycle selectors.

A further variation of the invention involves a two chambered pouch that contains one chemical solution in one chamber and another solution in the second chamber. Upon application of pressure through twisting or pressing, the solutions will mix within a third chamber, located within the contact end, thereby heating the surface of the contact end. In another embodiment two chemical solutions would be kept separately in a bottle. Upon spraying or pouring the solution onto the skin the chemical solutions get mixed, resulting in a chemical reaction that provides heat before reaching the skin surface. Strength of the solution would be predetermined such as to provide a specific temperature of a specific range of temperature in 46 C-62° C. The duration of heat is controlled by including in the solution alcohol or a similar chemical that will rapidly cool the surface within a brief predetermined time period. The end result is that the skin is rapidly heated to a temperature and then rapidly cooled.

An additional embodiment requires the use of a single chemical solution, located within an application vessel, to which a catalyst is added just prior to application. The catalyst may be positioned in a spray or pouring spout of the application vessel, such that the chemical solution must pass through the catalyst when the solution is either sprayed or poured. Upon spraying or pouring, the chemical solution in combination with the catalyst is mixed with oxygen in the atmosphere and a chemical reaction occurs providing heat at the skin surface. Still another embodiment would require the use of an electrical heater to heat a medical solution, volatile liquid, or gas to a specific temperature of a specific range of temperature in the range of 46-62° C., 49-62° C. or 50-69° C. The liquid may also become steam or gas in this temperature. The heated spray, heated medical solution, heated steam, or gas, is sprayed onto the skin either continuously or intermittently by manual or automatic operation. The head of the sprayer may be made small and long enough to facilitate the application of the heated spray onto the membrane inside the nose for treating itch within the nose. Thermostatic means for controlling the temperature of the spray or the liquid temperature are included in the sprayer.

The improvement method comprising heating a body heater as may be required to maintain said body heater at a substantially consistent temperature at and during the time of treatment of the skin area affected, said substantially uniform temperature being a predetermined temperature or a predetermined temperature range in ranges of about 49-69° C., 52-62° C., 52-69° C., 53-62° C., 50-62° C., 49-53° C., 54-56° C., 57-62° C., 50-70° C., or 56-62° C., and equal to a best effective temperature of a specific case; continually monitoring the temperature of the body heater to determine when and the degree of heat to be added to the body heater and to determine when adding of heat is to be discontinued; controlling the supply of power to the body heater in accordance with heat requirements determined by said temperature monitoring, and applying the body heater to the skin area that need treatment either continuously or discontinuously. Continually monitoring the temperature of the body heater within about +/−0.5° C. or +/−1° C. of said predetermined temperature, providing of selections of temperature, and indicating readiness to use will be included and these will help to eliminate edema, and rebound of itch. The body heater can be dry and wet, such as a wet ribbon heater or a wet towel heater.

Another improvement method comprising using a body heater to heat an skin area as may be required to maintain said skin area at a substantially constant temperature at and during the time of treating said skin area affected, said substantially uniform temperature being a predetermined temperature or a narrow range of temperature in ranges of about 49-69° C., 52-62° C., 52-69° C., 53-62° C., 50-62° C., 49-53° C., 54-56° C., 57-62° C., 50-70° C., or 56-62° C., and equal to a best effective temperature of a specific case; continually monitoring the temperature of the skin area to determine when and the degree of heat to be added to the skin area and to determine when adding of heat is to be discontinued; and controlling the supply of heating power to the skin area in accordance with heat requirements either manually or automatically, or determined by said temperature monitoring. Continually monitoring the temperature of the skin area within about +/−1° C. of said predetermined temperature will help to eliminate edema and rebound of itch. Heating the skin area discontinuously as monitored by a controlling means to heat the skin area to a specific narrow range of temperature in the above ranges and let the skin area to cool down to a tolerable temperature, repeating the heating and cooling until finishing the treatment, to avoid and minimizing any discomfort of heating the skin. The body heater can be dry and wet, such as a wet ribbon heater or a wet towel heater.

It will be apparent that improvements and modifications may be made within the purview of the invention without departing from the scope of the invention defined in the appended claims.

What is claimed is:

1. A method comprising:
   applying heat energy to skin affected by a specific skin condition via conduction of the heat energy from a heat application surface of a device, the heat application surface contacting the skin and being elevated to a selected temperature in a range of 46 to 62° C. or a range of 50 to 69° C. to treat the specific skin condition; and
   raising the temperature of the skin to clear up the skin condition.

2. The method of claim 1, further comprising maintaining the heat application surface at the selected temperature within a tolerance.

3. The method of claim 2, wherein the tolerance depends on the specific skin condition, and is selected from a group of tolerances consisting of +/−0.25° C., 0.5° C., 1° C., and 2° C.

4. The method of claim 2, wherein the tolerance is selected to prevent side effects.

5. The method of claim 4, wherein the side effects comprise edema, and rebound itch.

6. The method of claim 1, wherein the selected temperature is in a range of 46 to 62 degrees C.

7. The method of claim 6, wherein the selected temperature is about 50° C.

8. The method of claim 1, wherein the specific skin condition is acne.

9. The method of claim 1, wherein the specific skin condition is one or more of systemic skin itch, rash, eczema, psoriasis, hives, poison ivy, poison oak, dermatitis, and herpes.

10. The method of claim 1, further comprising indicating operational information visually and aurally.

11. The method of claim 10, wherein the operational information comprises system and temperature information.

12. The method of claim 1, wherein heat is applied to the skin in one or more pulses by controlling a supply of power to a heater in the device.

13. The method of claim 1, wherein heat is applied to the skin in one or more pulses.

14. A method comprising:
heating a skin area that has a skin condition using a heating device configured to heat the skin area to a predetermined temperature selected for treatment of the skin condition, the heating device comprising a heat application surface that is placed in contact with the skin and that conducts heat energy to the skin;
allowing the skin area to cool by decreasing the temperature of the heat application surface; and
repeating the heating and cooling for a period of time as required to treat the skin condition.

15. The method of claim 14, wherein the skin area is heated and allowed to cool by a pulsating application of heat from the device.

16. The method of claim 14, wherein the skin condition is selected from acne, rash, eczema, psoriasis, hives, poison ivy, poison oak, dermatitis, herpes, and systemic skin itching.

17. The method of claim 14, wherein the heat application surface is configured for a treatment option for a specific skin condition, an area of the body to be treated, and/or a patient type to be treated.

18. A method comprising:
choosing a treatment setting from a plurality of discrete treatment settings using a selector on a skin heating apparatus, the plurality of discrete treatment settings each provided to accommodate at least one of a specific skin condition, an area of a body to be treated, and a type of patient to be treated;
applying a heat application surface of the skin heating apparatus to a skin area having a specific skin problem, the heat application surface being heated to a treatment temperature corresponding to the chosen treatment setting by a heating element controlled by a control system, the treatment temperatures corresponding to the discrete treatment settings being in a range of 49 to 69° C.; and
introducing a therapeutically effective quantity of heat energy via the heat application surface to the skin area from the heat application surface having been heated to the treatment temperature of the chosen treatment temperature setting, such that the specific skin problem is effectively treated by the heat energy introduced by the heat application surface.

* * * * *